United States Patent [19]

Szabó et al.

[11] Patent Number: 5,008,386

[45] Date of Patent: Apr. 16, 1991

[54] METHYLATED CYCLODEXTRIN TYPE COMPOUNDS AND PROCESS FOR PREPARING SAME

[75] Inventors: Tibor Szabó; László Institóris; József Szejtli; Lajos Szente, all of Budapest; Ildikó Jod/e,acu/a/ l, Debrecen, all of Hungary

[73] Assignee: Chinoin Gyogyszer es Vegyeszeti Termekek Gyara RT., Budapest, Hungary

[21] Appl. No.: 256,857

[22] Filed: Oct. 12, 1988

[30] Foreign Application Priority Data

Oct. 13, 1987 [HU] Hungary ............... 4605/87

[51] Int. Cl.$^5$ ............... C08B 37/16
[52] U.S. Cl. ............... 536/103
[58] Field of Search ............... 536/103

[56] References Cited

U.S. PATENT DOCUMENTS 4,582,900 4/1986 Brandt et al. ............... 536/103
4,870,060 9/1989 Müller ............... 536/103

Primary Examiner—Ronald W. Griffin
Attorney, Agent, or Firm—Herbert Dubno; Jonathan Myers

[57] ABSTRACT

The invention relates to novel partially methylated carboxyacyl-cyclodextrins of the general formula (I),

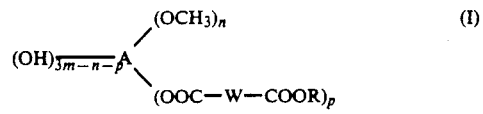

wherein A means the cyclodextrin skeleton of the general formula (II)

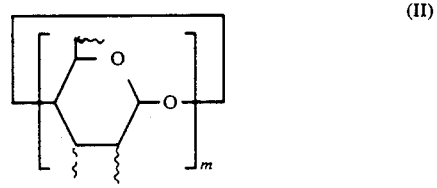

containing the substituents in the position labelled by the wavy line;
W stands for an alkylene, alkenylene or arylene group or the substituted derivatives thereof;
R means hydrogen, an alkyl, aryl or aralkyl group;
m is 6, 7 or 8;
n is an integer from 1 to 2m; and
p is $2m-n+z$, wherein the value of z is from 0 to 3 as well as their salts.

The novel derivatives induce less haemolytic effect than the cyclodextrin compounds used as starting materials.

8 Claims, No Drawings

METHYLATED CYCLODEXTRIN TYPE COMPOUNDS AND PROCESS FOR PREPARING SAME

FIELD OF THE INVENTION

The invention relates to novel ether-ester type methylated cyclodextrin (hereinafter abbreviated: CD) derivatives of the formula (I), $$(OH)_{3m-n-p}-A\begin{matrix}(OCH_3)_n\\ \\(OOC-W-COOR)_p\end{matrix}$$

wherein
A is the cyclodextrin skeleton of the formula (II)

containing the substituents in the positions labelled by the wavy lines;
W stands for an alkylene, alkenylene or arylene group or substituted derivatives thereof;
R means hydrogen, an alkyl, aryl or aralkyl;
m is 6, 7 or 8;
n is an integer from 1 to 2m; and
p is $2m-n+z$, wherein the value of z is from 0 to 3 as well as their salts.

The compounds of the formula (I) have negligible haemolytic effect while maintaining the advantageous properties of methylated cyclodextrins.

BACKGROUND OF THE INVENTION

Cyclodextrins (CD-s) and particularly their water-soluble derivatives increase the water-solubility of various drugs very significantly (in some cases by 2 to 3 orders of magnitude). Thus, their use is advantageous not only for enhancing the biological availability of orally administered drugs but also for improving the transdermal absorption of active agents and for the preparation of new "injectable" preparations.

However, in both of these latter fields of application essential requirements are a low level of local irritation and haemolytic activity. The haemolyzing effect of the various CD-s and their derivatives shows considerable differences. It is thus possible to prepare derivatives with an insignificant haemolyzing effect.

In low concentrations (5 mmol in the case of α-CD and 10 mmol in the case of γ-CD, respectively), CD-s protect the human erythrocytes against heat-induced or osmotic haemolysis whereas at higher concentrations (3 mmol of β-CD, 6 mmol of α-CD and 16 mmol of γ-CD, at 37° C. and pH 7,4 in 10 mmoles of an isotonic phosphate buffer), a haemolysis is induced. At these high concentrations, cholesterol is extracted from the cell membrane by CD-s (in an order of efficiency of β>γ>α), a fact indicating that the CD-induced haemolysis is a secondary phenomenon which is the consequence of an interaction between the CD-s and membrane components.

According to scanning electron microscope photographs, the protective action of CD-s below the critical concentrations mentioned above is due to the membrane expansion. It is likely that the fluidization of the membrane lipids is altered by CD-s whereby the erythrocytes are protected; however, these lipids are extracted from the membrane by higher CD concentrations, which lead to destruction of the membrane [J. Pharm. Dyn. 5, 741 (1982)].

In conclusion, it is desirable to prepare derivatives which make water-soluble various lipophilic active agents by complex formation, and react with the cell membrane lipids in such a way that their fluidity is decreased but that they are not extracted from the cell wall, i.e. the cell walls are not damaged and thus the erythrocytes are not haemolyzed.

Up to the present, four types of derivatives have been prepared for this purpose:

(a) Methylated CD-s, described abudantly in the literature are highly soluble and possess a high solution power (see German Patent No. 3,118,218), however their haemolytic effect is high (J. Szejtli: Cyclodextrin Technology, Ed. Reidel, Dordrecht, 1987).

(b) Acid-type ionic derivatives (carboxymethyl, sulfpropyl etc. compounds) have a lower haemolytic activity, but, their solution power is much weaker (J. Szejtli: Cyclodextrins and their Inclusion Complexes, Ed. Akademiai Kiadó, Budapest, 1982).

(c) The heterogeneous hydrophilic derivatives, e.g. hydroxypropyl-CD (European Patent No. 149,197) or soluble ionic CD polymers (Hungarian Patent No. 191,101) are scarcely haemolytic, but their preparation in a pure state is problematic. A further problem is the fate of the polymer in the organism, which has not been cleared up. These heterogeneous derivatives are not crystallizable so that their preparation in a technologically pure form requires expensive operations.

(d) Ethylated or dialkylaminoethylated and mixed ether derivatives can be characterized only by an average degree of substitution and are inhomogeneous, crystallizable substances (European Patents Nos. 146,841 and 147,685).

SUMMARY OF THE INVENTION

For eliminating the above disadvantages, ether-ester type methylated CD derivatives have been prepared and it has surprisingly been found that their haemolytic activity is insignificant.

The invention is based on the discovery that, in addition to the methyl groups, ester groups can be introduced with a very high selectivity into partially methylated CD-s by using dicarboxylic acids. In the thus prepared compounds, the dicarboxylic acid may be in a form of a free carboxylic group or in an esterified form. The salts of the thus prepared compounds are more soluble in water than dimethyl-CD and they do not precipitate from the aqueous solution on heating. Thus the complex can be sterilized by heat. Simultaneously, guest molecules containing basic groups result also in an ionic connection in addition to the apolar interaction with the CD cavity which is important for the solubility-increasing effect.

According to another aspect of the invention, there is provided a process for the preparation of partially methylated carboxyacylcyclodextrins of the formula (I), wherein A means the cyclodextrin skeleton of the formula (II) containing the substituents in the position labelled by the wavy line;

W stands for alkylene, alkenylene or arylene group or the substituted derivatives thereof;

R means hydrogen, an alkyl, aryl or aralkyl;

m is 6, 7 or 8;

n is an integer from 1 to 2m; and p is $2m-n+z$, wherein the value of z is from 0 to 3 as well as their salts, which comprises (a) reacting a partially methylated cyclodextrin of the formula (III)

$$(OH)_{3m-n}—A—(OCH_3)_n \qquad (III)$$

wherein A, m and n are as defined above, formula (IV),

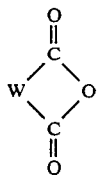

or with a dicarboxylic acid derivative of the formula (V),

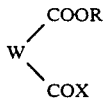

wherein X means a halogen or a carboxylate or phenolate group; or (b) reacting a mixture of cyclodextrins of the formula (III), partially methylated to various degrees, as defined above, with a dicarboxylic acid anhydride of the formula (IV), wherein W is as defined above, or with a dicarboxylic acid derivative of the formula (V), wherein R and X are as defined above in variant (a), separating by extraction the individual products from the resulting mixture of the compounds of the formula (I) containing various numbers of acyl groups and, if desired, esterifying the compound of the formula (I) thus obtained or converting it to its salt.

Even in the case of the defined degree of methylation, small amounts of several isomeric compounds may be present in the partially methylated CD-s depending on the position of the methyl groups. In the CD derivatives of the formula (I), the number of the acyloxy groups ("p") depends on the number of methoxy groups ("n") and on the isomerism ($p=2m-n+z$) which is taken into consideration by the additive member "z". When methyl groups are only in the 2- and 6-positions of the molecule and the 3-hydroxyl groups are not methylated, the value of "z" is zero.

According to the invention, the compounds of the formula (I) containing the desired number of acyl groups may be prepared in two days. According to an embodiment of the process of the invention, the CD-s are suitably methylated to give a product which is a mixture of compounds of the formula (III) which are methylated to various degrees and contain the product with the desired degree of methylation in the highest concentration. From this mixture, the CD with the desired grade of methylation is obtained in a convenient manner, e.g. by using column chromatography and is then selectively acylated to obtain the product containing the desired number of acyl groups.

Alternatively, the mixture obtained by methylation is acylated and then the product containing the desired number of acyl groups is separated from the reaction mixture in a suitable way, e.g. by purifying with extraction.

The partially methylated CD-s of the formula (III) used as starting materials can be prepared by a suitable modification of known methylating procedures in such a way that the amounts of the reactants are chosen according to the desired grade of methylation whereas the time of the reaction is controlled by continuously following the reaction, by using thin layer chromatography (hereinafter abbreviated: TLC).

The methylation is preferably carried out in dimethylsulfoxide, dimethylformamide or in their mixture. Barium hydroxide, barium oxide, sodium hydroxide or a mixture thereof are suitable acid binding agents. Dimethyl sulfate or methyl iodide can preferably be employed as methylating agents. Among a number of TLC developing systems, a 100:25:20 mixture of acetone/diisopropyl ether/25% ammonium hydroxide on Merck Kieselgel-60 $F_{254}$ HPTLC sheets of 10 cm in size can preferably be used for following the reaction. The development is carried out by using a 5:95 mixture of concentrated sulfuric acid/methanol at 110° C.

In the system described above, spots with the following $R_f$ values appear in course of the methylation of e.g. β-CD: 0.05; 0.10; 0.12; 0.19; 0.21; 0.30; 0.32; 0.40; 0.43; 0.48; 0.51; 0.57 and 0.63. The spot with $R_f$ value of 0.63 corresponds to the known heptakis (2,6-di-O-methyl)-β-CD whereas the β-CD starting material remains on the start line.

The maximum of the concentration distribution proceeds in parallel with the progress of the reaction.

The reaction mixture may preferably be worked up by extraction with an organic solvent and water. By a suitable selection of the sodium chloride concentration of the aqueous phase and the type of the organic solvent, the resulting products with a various grade of methylation can partially be separated.

Thus, by using e.g. ethyl acetate, the products having an $R_f$ value over 0.3 only can be extracted from the above mixture; whereas by using chloroform, the products having an $R_f$ value below 0.3 can also be obtained. Products with a defined degree of methylation can be separated in a uniform pure state by using column chromatography. The product isolated by chromatography may further be purified by recrystallization from an organic solvent and/or water.

According to the invention, the acylation of the partially methylated CD-s of the formula (III) with the reactants of the formula (IV) or (V), respectively, is carried out under the usual conditions, in anhydrous solvents in the presence of an acid binding base and, if desired, in the presence of a catalyst. Ethers, halogenated hydrocarbons, aromatic hydrocarbons, pyridine, dipolar aprotic solvents or mixtures thereof may preferably be used as reaction media. Pyridine or trialkylamines may suitably be employed as acid binding agents. The acylating reaction may significantly be accelerated by dialkylaminopyridine compounds.

The temperature and duration of the reaction is regulated with consideration of the reactivity of the acylating agent used.

The progress of the reaction is followed by using TLC method. Suitable developing agents are a 100:25:20 mixture of acetone/diisopropyl ether/25% ammonium hydroxide or a 100:10:25 mixture of acetone/methanol/25% ammonium hydroxide. The reaction mixture is worked up by extraction with an organic solvent and water. In the case of product containing a free carboxyl group [compounds of the formula (I) containing hydrogen as R], it is suitable to form first a water-soluble salt (e.g. by using sodium hydrogen carbonate) and then to remove all non-acidic concomitant substances by washing with an organic solvent. Thereafter the pH of the aqueous phase is adjusted to the appropriate value by adding a mineral acid and the product is obtained by extracting it into an organic solvent. When a CD mixture containing members with various degrees of methylation is used as starting material which results in a mixture of monoacyl, diacyl etc. products containing various numbers of acyl groups, then the pH value of the aqueous solution is gradually decreased and thus, the products with various degrees of methylation can be separated and isolated with a significant selectivity.

The organic extracts are dried and the solvent is evaporated under reduced pressure to obtain the crude product in a white, well pulverizable, amorphous foam form.

If desired, the crude product may further be purified by recrystallization from an organic solvent (e.g. from a mixture of ethyl acetate and hexane) or from water.

The quality of the product thus obtained is examined by TLC, $^1$H-NMR spectrum, titration and melting point determination.

If desired, the free carboxyl group of the methylated carboxy-acyl-CD-s can be esterified by using diazomethane under anhydrous conditions.

SPECIFIC EXAMPLES

The invention is illustrated in detail by the following non limiting Examples 1 to 7. The investigation of the haemolytic effect is described in Example 8, the examination of the solubility-increasing effect is reported in Example 9.

EXAMPLE 1

Preparation of a target product with a methylation grade of 13 by the partial methylation of β-cyclodextrin In a flask of 500 ml volume, the mixture of 22.6 g (20 mmol) of β-CD in 160 ml of dimethylformamide (hereinafter abbreviated: DMF) is stirred at room temperature until complete dissolution, then cooled to 0° C. At the same temperature, 44.2 g (140 mmol) of barium hydroxide, 12.9 g (84 mmol) of barium oxide and 30 ml (480 mmol) of methyl iodide are added to the above solution under stirring. The reaction mixture is stirred at a temperature between 0° C. and 5° C. while taking a sample in each hour and following the reaction by using TLC. The chromatography is carried out on a Merck Kieselgel-60 $F_{254}$ HPTLC sheet of 10 cm in size by using a 100:25:20 mixture of acetone/diisopropyl ether/25% ammonium hydroxide as developing agent. After stirring for 8 to 10 hours, the substance having an $R_f$ value of 0.51 is present in the highest concentration in the reaction mixture. The reaction is stopped by adding 70 ml of water and 150 ml of saturated sodium chloride solution and the product is extracted from the aqueous solution by shaking 3 times with 200 ml of ethyl acetate each.

After combining, the ethyl acetate solution is successively washed twice with 50 ml of saturated sodium chloride solution each, then 3 times with 50 ml of saturated sodium sulfate solution each, then dried over anhydrous sodium sulfate. After filtering off the drying agent and evaporating the filtrate under reduced pressure, 20.5 g of crude product are obtained in the form of a well-pulverizable white foam. Based on chromatography in the above system, this crude product contains: 50% of trideca-O-methyl-β-CD with an $R_f$ value of 0.48 to 0.51; about 25% of heptakis(2,6-di-O-methyl)-β-CD with an $R_f$ value of 0.63; and about 25% of dodeca-O-methyl-β-CD with an $R_f$ value of 0.40–0.43. From the crude product, the individual components are separated in a pure form by column chromatography. For this purpose, a column is prepared by using 1 kg of Merck Kieselgel-60 silicagel with a 0.06 to 0.2 mm particle size in a 10:1 benzene/methanol mixture. The crude product is dissolved in 40 ml of chloroform and poured onto the column. The products are successively eluated by using 104 ml of a 10:1 mixture of benzene/methanol. The chromatography is followed by TLC. The fractions containing an uniform product are evaporated under reduced pressure to give the following amorphous, white, powder-like products:

Heptakis(2,6-di-O-methyl)-β-CD: 4.2 g
Trideca-O-methyl-β-CD: 9.4 g
Dodeca-O-methyl-β-CD: 4.9 g If desired, the products obtained after chromatography are further purified by recrystallization. 9 g of trideca-O-methyl-β-CD are dissolved in 27 cm of hot ethyl acetate, 54 ml of n-hexane are added dropwise to under stirring, then the obtained crystalline mass is cooled to 0° C. The crystals are filtered, washed with a mixture of ethyl acetate and hexane and dried to a constant weight to give 7.8 g of a white crystalline substance.

7 g of the product crystallized from ethyl acetate/hexane are dissolved in 28 ml of cold water, then 14 ml of water are distilled off under reduced pressure and the remaining crystalline mass is heated to 95° C. the crystalline product is filtered on a filter preheated to 95° C. and dried to constant weight. Thus, 4.9 g of a white crystalline substance are obtained, m.p.: 270°–280° C. (with decomposition).

EXAMPLE 2

Preparation of trideca-O-methyl-monosuccinyl-β-cyclodextrin (SUMEB)

In a flask of 250 ml volume, 13.2 g (10 mmol) of trideca-O-methyl-β-CD (prepared as described in Example 1 and purified by column chromatography) are stirred with 130 ml of anhydrous tetrahydrofuran (abbreviated hereinafter: THF) until dissolution, then 10 ml (7.2 mmol) of triethylamine, 4.0 g (40 mmol) of succinic acid anhydride and 0.49 g (4 mmol) of dimethylaminopyridine as catalyst are added. The reaction mixture is heated to 50° C. and stirred for 10 hours. Thereafter, 300 ml of 1M sodium hydrogen carbonate solution, 25 g of sodium chloride and 200 ml of ethyl acetate are added to the reaction mixture. After stirring for a short time, the aqueous and organic phases are separated. The aqueous phase is again washed with 200 ml of ethyl acetate. After separation, 50 g of sodium chloride are dissolved in the aqueous phase and the pH value is adjusted between 7 and 8 by adding 50 ml of 2N sodium hydrogen sulfate solution.

The product is extracted 4 times with 300 ml of ethyl acetate each. After combining, the ethyl acetate solution is washed with 200 ml of saturated sodium chloride plus 50 ml of 2N sodium hydrogen sulfate solution and then 3 times with 200 ml of saturated sodium chloride solution each. The organic phase is dried over sodium sulfate, filtered and evaporated to dryness under reduced pressure. The obtained solid white foam is put on a tray and dried to constant weight to give 12.7 g of product.

This crude product is dissolved in 38 ml of hot ethyl acetate, then 76 ml of diisopropyl ether are portionwise added to the solution under stirring. The crystalline mass is cooled to 0° C., filtered, washed and dried to give 10.3 g of a white crystalline substance which may further be purified by recrystallization from water in the following way.

10.3 g of product are dissolved in 40 ml of water, then 20 ml of water are distilled off under reduced pressure. The residue is heated to 95° C. under stirring and the crystalline mass is filtered onto a filter preheated to 95° C. The filtered crystals are washed with hot water and dried to constant weight to obtain 7.2 g of a white crystalline substance.

TLC examination:
on Merck, Kieselel-61 $F_{254}$ HPTLC sheet of 10 cm in size; E-1 developing system: 100:25:20 mixture of acetone/diisopropyl ether/25% ammonium hidroxide;
E-2 developing system: 100:10:25 mixture of acetone/methanol/25% ammonium hydroxide
Detection: by a 95:5 mixture of methanol/sulfuric acid at 110° C.
$R_f$ values:
in the E-1 system: 0.16, one spot
in the E-2 system: 0.50, one spot
$^1$H-NMR:
C(1)—H+C(3)—OH: 5.0 ppm
skeletal protons: 3–4.5 ppm 96 protons
C(2)—OCH$_3$ and C(6)—OCH$_3$: 3.65 and 3.42 ppm
OOC—(CH$_2$)$_2$—COO: 2.65 ppm 4 protons
Melting point:
270°–280° C. (with decomposition)

Two signals appearing in the $^{13}$C-NMR spectrum at 173.49 and 172.01 ppm are the two carbonyl carbon signals of the succinyl group: the former one can be assigned to the free carboxyl group whereas the latter one can be assigned to the ester-carbonyl group. The signals from 82.22 to 80.57 ppm belong to the C$_2$ atom; those from 73.65 to 72.39 ppm to the C$_5$ atom; those from 71.70 to 71.21 ppm to the C$_6$ atom. The very intense signal appearing at 70.36 ppm is assigned to the free C$_3$—O—H: The signals appearing at 60.28 and 60.19 ppm belong to the methyl groups on the C$_2$ atom; those appearing from 58.95 to 57.89 ppm can be assigned to the methyl groups at C$_6$. Both signals appearing with a nearly equal intensity at 28.90 and 28.42 ppm belong to the two methylene groups of the succinyl group: the former one can be assigned to the carbon atom next to the ester-carbonyl group whereas the latter one belongs to the carbon atom next to the free carboxyl group.

EXAMPLE 3

Preparation of trideca-O-methyl-monomaleinyl-$\beta$-cyclodextrin (MAMEB)

The reaction is carried out as described in Example 2, except that 3.9 g (40 mmol) of maleinic acid anhydride are used instead of the succinic acid anhydride.

After termination of the reaction, 300 ml of 1M sodium hydrogen carbonate solution and 25 g of sodium chloride are added to the black tarry reaction mixture which is then washed twice with 200 ml of ethyl acetate each. After separation, 75 g of sodium chloride and 80 ml of 2N sodium hydrogen sulfate solution are added to the aqueous phase and the product is extracted 4 times with 300 ml of ethyl acetate each. The combined ethyl acetate solution is washed with 200 ml of saturated sodium chloride solution plus 50 ml of 2N sodium hydrogen sulfate solution and then 3 times with 200 ml of saturated sodium chloride solution each. The organic phase is dried over sodium sulfate, filtered and evaporated to dryness under reduced pressure to give 9.6 g white solid foam-like product.

TLC examination:
as described in Example 2.
$R_f$ values:
in the E-1 system: 0.22, one spot
in the E-2 system: 0.61, one spot
$^1$H-NMR:
C(1)—H+C(3)—OH : 5.0 ppm
Skeletal protons : 3–4.5 ppm 96 protons
C(2)—OCH$_3$ and C(6)—OCH$_3$ : 3.68 and 3.45 ppm
OOC—CH=CH—COO : 6.42 and 6.32 ppm 2 protons
Melting point:
165°–167° C.

EXAMPLE 4

Preparation of trideca-O-methyl-monophthalyl-$\beta$-cyclodextrin (FTAMEB)

The reaction is carried out as described in Example 2, except that 5.9 g (40 mmol) of phthalic acid anhydride are used instead of succinic acid anhydride.

After termination of the reaction, 300 ml of 1M sodium hydrogen carbonate solution are added to the reaction mixture which is then washed twice with 200 ml of ethyl acetate each. After separation, 100 g of sodium chloride are dissolved in the aqueous phase and the product is extracted 3 times with 300 ml of ethyl acetate each. The ethyl acetate phases are combined, then washed, dried and evaporated as described in Example 2 to give 13.6 g of a white solid foam-like product.

TLC examination:
as described in Example 2.
$R_f$ value:
in the E-1 system: 0.29, one spot
in the E-2 system: 0.70, one spot
$^1$H-NMR:
C(1)—H+C(3)—OH : 5.00 ppm
Skeletal protons : 3–4.5 ppm 96 protons
C—(2)—OCH$_3$+C(6)—OCH$_3$ : 3.65 and 3.44; 3.35 ppm
Aromatic protons : 7.76 4 protons
Melting point:
167°–170° C.

EXAMPLE 5

Preparation of dodeca-O-methyl-disuccinyl-β-cyclodextrin (DISUMEB)

In a flask of 250 ml of volume, 13.3 g (10 mmol) of dodeca-O-methyl-β-CD prepared as described in Example 1 and purified by column chromatography are stirred with 130 ml of anhydrous THF until complete dissolution, then 20 ml (14.4 mmol) of triethylamine, 8.0 g (80 mmol) of succinic acid anhydride and 0.98 g (8 mmol) of dimethylaminopyridine as catalyst are added. The reaction mixture is stirred at 50° C. for 10 hours. After disappearance of the starting material (as detected by TLC), the mixture is cooled down and 300 ml of 1M sodium hydrogen carbonate solution and then 100 g of sodium chloride are added. The resulting solution is washed twice with 200 ml of ethyl acetate each, then 130 ml of 2N sodium hydrogen sulfate solution are added to the solution and the product is extracted 4 times with 300 ml of ethyl acetate each. The combined ethyl acetate solution is washed first with 200 ml of saturated sodium chloride solution plus 50 ml of 2N sodium hydrogen sulfate solution, then 3 times with 200 ml of saturated sodium chloride solution each. The organic phase is dried over sodium sulfate, filtered and evaporated to dryness under reduced pressure to give 13.1 g of a white solid foam-like product.

TLC examination:
as described in Example 2.
$R_f$ values:
in the E-1 system: 0.03
in the E-2 system: 0.26
$^1$H-NMR:
C(1)—H+C(3)—OH : 5.00 ppm
Skeletal protons : 3–4.5 ppm 94 protons
C(2)—OCH$_3$ and C(6)—OCH$_3$ : 3.65 and 3.42 ppm
OOC—(CH$_2$)$_2$—COO : 2.65 ppm 8 protons

EXAMPLE 6

Preparation of trideca-O-methyl-monosuccinyl-β-cyclodextrin and dodeca-O-methyl-disuccinyl-β-cyclodextrin 14 g of a crude product prepared according to Example 1, which consists of a mixture of β-CD-s with a methylation grade of 12, 13 or 14, respectively, are dissolved in 130 ml of anhydrous THF in a flask of 250 ml volume and the reaction is carried out as described in Example 2. After termination of the reaction, 300 ml of 1M sodium hydrogen carbonate solution and 25 g of sodium chloride are added to the reaction mixture and the unchanged heptakis(2,6-di-O-methyl)-β-CD is washed out 3 times with 200 ml of ethyl acetate each. Then, 75 g of sodium chloride and 50 ml of 2N sodium hydrogen sulfate solution are added to the aqueous phase which is then extracted 4 times with 300 ml of ethyl acetate each. The combined ethyl acetate solution is washed with 200 ml of saturated sodium chloride solution plus 50 ml of 2N sodium hydrogen sulfate solution and then 3 times with 200 ml of saturated sodium chloride solution each.

After drying, the organic phase is evaporated to dryness under reduced pressure to give 5.2 g of white, powder-like trideca-O-methyl-monosuccinyl-β-CD.

After adding 40 ml of 2N sodium hydrogen sulfate solution, the aqueous phase is washed with 200 ml of ethyl acetate for removing the residual monosuccinyl product.

After adding a further amount of 40 ml of 2N sodium hydrogen sulfate solution, the aqueous phase is extracted 3 times with 300 ml of ethyl acetate each. The combined ethyl acetate solution is washed, dried and evaporated to dryness as described above. Thus, 2.8 g of white, powder-like dodeca-O-methyl-disuccinyl-β-CD are obtained.

EXAMPLE 7

Preparation of trideca-O-methyl-monosuccinyl-β-cyclodextrin methyl ester

To a solution of 1.42 g (1 mmol) of trideca-O-methyl-mono-succinyl-β-CD (prepared as described in Example 2) in 2.8 ml of anhydrous THF, 7 ml (2.1 mmol) of ethereal diazomethane solution are added. The reaction becomes complete after stirring for 15 minutes in a cold water bath. Then, the reaction mixture is evaporated to dryness under reduced pressure to give 1.43 g of amorphous powder.

$R_f$ value in the E-1 system: 0.69
$^1$H-NMR: —COOCH$_3$: 3.8 ppm

EXAMPLE 8

Investigation of the haemolytic effect

Solutions containing the test substances in 10 mM concentration were prepared in a 10 mM phosphate buffer at pH 7.4. The commercially available α-, β- and γ-CD products manufactured by Chinoin Chemical and Pharmaceutical Works Ltd. (Budapest, Hungary) were used.

DIMEB and TRIMEB, i.e. heptakis(2,6-di-O-methyl)-β-CD and heptakis(2,3,6-tri-O-methyl)-β-CD, respectively were prepared by the partial or total methylation of β-CD as described previously.

Preparation of the erythrocytes

Fresh human blood (taken from healthy donors being under no medicinal treatment) treated by citrate as anticoagulant was centrifuged at 2000–3000× g for 10 minutes, then the supernatant was decanted, the erythrocytes were suspended in 5 ml of 10 mM isotonic phosphate buffer each and again centrifuged at 2000–3000× g for 10 minutes. After repeating twice this operation, the resulting erythrocytes were suspended in isotonic phosphate buffer to obtain a haematocrite volume of about 10%. This suspension (which could be stored in a refrigerator at about 4° C. for at most 48 hours) was used in further experiments.

Method of the measurement 0.4 ml of erythrocyte suspension was added to a test solution of 4 ml total volume containing the tested CD-s and derivatives in various concentrations, then the mixture was incubated at 37° C. for 30 minutes. The mixture of 4 ml isotonic phosphate buffer and 0.4 ml erythrocyte suspension was used as blank trial (which was treated similarly to the samples).

After 30 minutes, the suspensions being present in the centrifuge tubes were centrifuged at 250–500× g for 10 minutes. (It was observed that no transparent supernatant, useful for spectrophotometric determination was obtained when the centrifuging was carried out for a shorter time.) After 10 minutes, the supernatants were drained off and their extinction was photometrically determined at 543 nm against a blank solution. In order to give the percentage of haemolysis, the extinction measured after a complete haemolysis had to be determined. This value was obtained in such a way that 0.4 ml of erythrocyte suspension was added to 4 ml of distilled water, then incubation and centrifuging were carried out in the same manner as described for the samples. The extinction of the solution thus obtained gave the 100% value of the haemolysis; when relating the measured extinctions of the samples to the 100% value, the extent of the haemolysis was obtained as a relative percentage.

RESULTS

Unsubstituted cyclodextrins:

α-CD: No haemolytic effect was observed in a concentration of 6 mM (corresponds to 5.8 mg/ml); a haemolysis value of 50% was observed in a concentration of 12 mM (corresponds to 11.7 mg/ml).

β-CD: NO haemolytic effect was observed in a concentration of 1.6 mM (1.8 mg/ml); a haemolysis value of 50% was observed in a concentration of 6 mM (6.8 mg/ml); a haemolysis value of 100% was observed in a concentration of 9 mM (10 mg/ml).

γ-CD: Practically no haemolytic effect was observed up to a concentration of 9 mM (11 mg/ml); a haemolysis value of 50% was observed in a concentration of 24 mM (32 mg/ml); a haemolysis value of 100% was observed in a concentration of 33 mM (44 mg/ml).

TABLE I

The haemolytic effect of substituted cyclodextrins

| CD concentration mg/ml | Haemolysis values measured % | Average % |
|---|---|---|
| α CD | | |
| 1.105 | 0.69 | 0.69 |
| 2.209 | 3.54, 4.77, 4.8, 4.97, 4.36 | 4.48 ± 0.9 |
| 5.523 | 5.58, 4.12 | 4.85 ± 0.7 |
| 6.159 | 5.16 | 5.16 |
| 6.627 | 5.36, 4.97 | 5.165 ± 0.2 |
| 7.73 | 6.79 | 6.79 |
| 8.836 | 13.8, 8.009, 11.09 | 10.96 ± 2.8 |
| 11.045 | 15.83 | 15.8 |
| 12.318 | 86.77, 91.77 | 89.27 ± 2.5 |
| 15.397 | 100 | 100 |
| β -CD | | |
| 1.288 | 4.4 | 4.4 |
| 2.577 | 7.34, 10.1 | 8.72 ± 1.5 |
| 3.865 | 15.31, 15.14 | 15.22 ± 0.1 |
| 5.154 | 19.57, 25.00 | 22.28 ± 2.7 |
| 6.442 | 50.58, 49.63 | 50.1 ± 0.1 |
| 9.019 | 68.08, 71.12 | 69.6 ± 1.5 |
| 10.308 | 96.48, 96.40, 100.0 | 97.6 ± 2.4 |
| γ -CD | | |
| 1.472 | 0.88 | 0.88 |
| 2.945 | 3.68, 4.8 | 4.24 ± 0.6 |
| 4.417 | 4.21, 3.74 | 3.97 ± 0.2 |
| 5.89 | 6.42, 6.49, 4.21 | 5.7 ± 1.7 |
| 7.363 | 3.54, 3.16 | 3.35 ± 0.2 |
| 8.835 | 7.17, 5.97, 4.8 | 5.98 ± 1.2 |
| 10.307 | 9.48, 8.89 | 9.18 ± 0.3 |
| 11.78 | 4.93, 4.62, 4.8, 5.38 | 5.38 ± 1.0 |
| 14.72 | 10.54, 14.86 | 12.7 ± 2.1 |
| 22.08 | 20.66 | 20.66 |
| 29.44 | 64.19 | 64.19 |
| 36.8 | 68.65, 79.83 | 74.24 ± 5.5 |
| 44.16 | 100.00 | 100.00 |

Methylated cyclodextrins

The methylated CD-s show a higher haemolytic effect than that of the β-CD mother compound. Under the given circumstances the same percentage of haemolysis induced by β-CD appears at the one sixth concentration of DIMEB. In the case of TRIMEB, the displacement of the concentration is not so high, however, in a given concentration the haemolytic effect of TRIMEB is also higher than that of the mother compound.

DIMEB: No haemolytic effect was observed in a concentration of 0.22 mM (0.3 mg/ml); a haemolysis value of 50% was observed in a concentration of 1.0 mM (1.44 mg/ml); a haemolysis value of 100% was observed in a concentration of 1.5 mM (2.2 mg/ml).

TRIMEB: No haemolytic effect was observed in a concentration of 1.4 mM (2.0 mg/ml); a haemolysis value of 50% was observed in a concentration of 4 mM (5.7 mg/ml); a haemolysis value of 100% was observed in a concentration of 6 mM (8.5 mg/ml).

TABLE II

The haemolytic effect of methylated cyclodextrins

| CD concentration mg/ml | Haemolysis values measured % | Average % |
|---|---|---|
| DIMEB | | |
| 0.303 | 0.75, 0.63 | 0.69 ± 0.15 |
| 0.909 | 17.55, 16.58 | 17.06 ± 0.5 |
| 1.212 | 44.84 | 44.84 |
| 1.516 | 51.38, 58.49 | 54.93 ± 3.5 |
| 1.819 | 82.66, 87.5 | 85.08 ± 2.5 |
| 2.122 | 93.44 | 93.44 |
| 2.425 | 96.73, 96.6 | 96.65 ± 0.05 |
| 3.032 | 100.00 | 100.00 |
| TRIMEB | | |
| 0.325 | 0.00 | 0.00 |
| 0.65 | 0.44 | 0.44 |
| 0.90 | 0.44 | 0.44 |
| 2.60 | 6.3, 6.05 | 6.15 ± 0.15 |
| 3.25 | 15.19 | 15.19 |
| 4.875 | 43.79 | 43.79 |
| 6.50 | 58.5 | 58.5 |
| 9.75 | 69.5 | 69.5 |

The haemolytic effects of the partially methylated β-CD derivatives are between the haemolytic effect of the unsubstituted β-CD and that of the pure DIMEB.

The haemolytic effect of trideca-O-methyl-monosuccinyl-β-CD (SUMEB) was significantly lower in comparison to the haemolytic effect of the mother compound.

No haemolytic effect was observed at 0.3 mg/ml concentration of either of the compounds; trideca-O-methyl-monosuccinyl-β-CD gave a haemolysis value of 10% in a concentration of 2 mg/ml whereas a similar concentration of the mother compound induced a value higher than 90%.

A haemolysis value of 50% was observed at a 6.5 mg/ml concentration of trideca-O-methyl-monosuccinyl-β-CD.

Trideca-O-methyl-monosuccinyl-β-cyclodextrin methyl ester:

It has been supposed that, when the decrease in the haemolytic effect is due to the presence of the charge-bearing group, then the product obtained by the methylesterifycation of trideca-O-methyl-monosuccinyl-β-CD would again show a higher haemolysis value. However, the haemolytic effect of the methylesterified trideca-O-methyl-monosuccinyl-β-CD is not significantly different from the haemolytic effect of the trideca-O-methyl-monosuccinyl-β-CD.

TABLE III

The haemolytic effect of succinyl-DIMEB and methylated succinyl-DIMEB

| CD concentration mg/ml | Haemolysis values measured % | Average % |
|---|---|---|
| Succinyl-DIMEB | | |
| 0.5 | 1.72, 2.29 | 2.005 ± 0.3 |
| 1.25 | 3.06, 5.83, 5.32 | 4.79 ± 1.7 |
| 2.0 | 11.95, 9.16 | 10.55 ± 1.4 |
| 2.5 | 21.02, 16.99 | 19.005 ± 2.01 |
| 5.0 | 36.99, 30.72 | 33.31 ± 3.7 |
| 7.5 | 68.93, 62.59 | 65.76 ± 3.2 |
| Succinyl-DIMEB methyl ester | | |
| 0.25 | 0.68 | 0.68 |
| 1.25 | 4.61, 5.62, 4.74 | 4.99 ± 0.65 |
| 2.5 | 15.72, 14.00 | 14.86 ± 0.86 |
| 5.0 | 27.24, 17.92 | 22.58 ± 4.66 |
| 6.25 | 32.86 | 32.86 |

EXAMPLE 9

Investigation of the solubility-increasing effect

Comparison of the solubility-increasing effect of trideca-O-methyl-monosuccinyl-$\beta$-cyclodextrin (SUMEB) with that of heptakis(dimethyl-$\beta$-cyclodextrin (DIMEB)

Based on the structure of SUMEB, it may be supposed that, in addition to the inclusion complex formation, in the case of guest molecules containing a basic functional group, the acid-base interaction may be a component of the host-guest connection formed in an aqueous solution which may result in an enhanced solubility-increasing effect in comparison to that of DIMEB when this supposition is right. Therefore comparative examinations concerning the solubility-increasing effect were performed with model guest-molecules containing a basic group. The results of these examinations are summarized in the following Table. (The measurements were carried out by UV spectrophotometry at 22° C. after stirring for 18 hours).

| Substrate | Solubility (mg/ml) in water | in a 2.5% DIMEB solution | in a 2.5% SUMEB solution | SUMEB DIMEB |
|---|---|---|---|---|
| ± Prenylamine base | 0.31 | 2.0 | 7.5 | 3.75 |
| ± Verapamil base | 0.27 | 4.93 | 11.0 | 2.24 |
| − N-Methylephedrine base | — | 18.5 | 22.0 | 1.2 |
| ± Sensit base | 2.1 | 5.5 | 8.5* | 1.53* |
| Lidocaine base | 4.0 | 6.6 | 9.5 | 1.43 |
| Triamcinolone | 0.19 | 66.0 | 38.2 | 0.57 |
| Diphenylamine | — | 0.52 | 0.41 | 0.72 |
| Hydrocortisone | 0.45 | 8.0 | 3.2 | 0.38 |
| Cholesterol | 0.1 | 1.71 | 0.64 | 0.37 |

*The UV maxium shifted under the effect of SUMEB

What is claimed is:

1. A partially methylated carboxyacyl-cyclodextrin of the formula (I), $$(OH)_{3m-n-p}-A{\Large\begin{matrix}(OCH_3)_n\\(OOC-W-COOR)_p\end{matrix}} \quad (I)$$

wherein

A means the cyclodextrin skeleton of the formula (II)

$$\left[\begin{matrix}\text{pyranose ring with O}\end{matrix}\right]_m \quad (II)$$

containing the substituents in the position labelled by the wavy line;

W stands for an alkylene, alkenylene or arylene group;

R means hydrogen, alkyl, aryl or aralkyl;

m is 6, 7 or 8;

n is an integer from 1 to 2m; and p is 2m−n+z, wherein the value of z is from 0 to 3 with the proviso that p does not equal 0 or a salt thereof.

2. A process for the preparation of a partially methylated carboxyacyl-cyclodextrin of the formula (I), $$(OH)_{3m-n-p}-A{\Large\begin{matrix}(OCH_3)_n\\(OOC-W-COOR)_p\end{matrix}} \quad (I)$$

wherein

A means the cyclodextrin skeleton of the formula (II)

$$\left[\begin{matrix}\text{pyranose ring with O}\end{matrix}\right]_m \quad (II)$$

containing the substituents in the position labelled by the wavy line;

W stands for an alkylene, alkenylene or arylene group;

R means hydrogen, alkyl, aryl or aralkyl;

m is 6, 7 or 8;

n is an integer from 1 to 2m; and p is 2m−n+z, wherein the value of z is from 0 to 3, with the proviso that p does not equal 0 or a salt thereof, which comprises (a) reacting a partially methylated cyclodextrin of the formula (III)

$$(OH)_{3m-n}-A-(OCH_3)_n \quad (III)$$

wherein A, m and n are as defined above, with a dicarboxylic acid anhydride of the formula (IV), $$\begin{matrix}O\\\parallel\\C\\W{\Large\diagup}\quad{\Large\diagdown}O\\\quad C\\\quad\parallel\\\quad O\end{matrix} \quad (IV)$$

wherein W is as defined above, or with a dicarboxylic acid derivative of the formula (V),

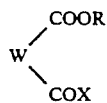 (V)

wherein R is as defined above and X means halogen or a carboxylate or phenolate group; or (b) reacting a mixture of cyclodextrins of the formula (III), partially methylated to a various degree, wherein A, m and n are as defined above, with a dicarboxylic acid anhydride of the formula (IV), wherein W is as defined above, or with a dicarboxylic acid derivative of the formula (V), wherein R and X are as defined above, separating by extraction the individual products from the resulting mixture of the compounds of the formula (I) containing various number of acyl groups to obtain the compounds of the formula (I) where R is hydrogen, and to obtain the compound of the formula (I) where R is alkyl, aryl or aralkyl, esterifying the compound of the formula (I) where R is hydrogen.

3. The process as claimed in claim 2, which comprises carrying out the reaction in an organic anhydrous solvent.

4. The process as claimed in claim 2, which comprises using an acid binding agent.

5. The process as claimed in claim 2, which comprises purifying the crude product by using extraction with ethyl acetate, column chromatography, or crystallization.

6. A process as claimed in claim 2, variant (b), which comprises separating the individual products from the mixture of compounds of the formula (I) containing various number of acyl groups by using extraction with ethyl acetate at various pH values.

7. The partially methylated carboxyacyl cyclodextrin of the Formula (I) defined in claim 1 wherein m is 7, n is 12 or 13, p is 1 or 2, and 3m—-n—p is 7, and W and R are as defined above, or a salt thereof.

8. The partially methylated carboxyacyl cyclodextrin of the Formula (I) defined in claim 1 which is selected from the group consisting of:
(a) trideca-O-methyl-monosuccinyl-beta-cyclodextrin or the methyl ester thereof;
(b) trideca-O-methyl-monomaleinyl-beta-cyclodextrin;
(c) trideca-O-methyl-monophthalyl-beta-cyclodextrin; and
(d) dodeca-O-methyl-disuccinyl-beta-cyclodextrin; or a salt thereof.

* * * * *